United States Patent [19]

Purcell et al.

[11] Patent Number: 4,549,883
[45] Date of Patent: Oct. 29, 1985

[54] CETANE IMPROVER FOR DIESEL FUEL

[76] Inventors: Robert F. Purcell, 605 Bryce Trail, Roselle, Ill. 60172; Louis L. Hallock, Rte. No. 3, Miller Rd., P.O. Box 271, Lake Zurich, Ill. 60047

[21] Appl. No.: 563,124

[22] Filed: Dec. 19, 1983

[51] Int. Cl.$^4$ .............................................. C10L 1/22
[52] U.S. Cl. ...................................................... 44/57
[58] Field of Search ...................................... 44/56, 57

[56] References Cited

U.S. PATENT DOCUMENTS 2,241,492  5/1941  Vanderbilt ............................. 44/57
2,274,629  2/1942  Ellis ......................................... 44/57
4,417,903  11/1983 Hinkamp ................................. 44/57

Primary Examiner—Y. Harris-Smith
Attorney, Agent, or Firm—Leydig, Voit & Mayer, Ltd.

[57]  ABSTRACT

Hydrocarbon-based fuel compositions which provide improved cetane ratings and a method of making them which comprises admixing a major amount of a petroleum fraction of the diesel boiling range and a small, effective amount of at least one compound having the general formula:

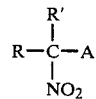

where
R is H, CH$_3$ or A;
R' is H, CH$_3$ or C$_2$H$_5$;
A is

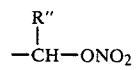

or is

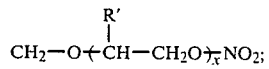

R" is H or C$_{1-3}$ alkyl; and
x is 1 or 2.

6 Claims, No Drawings

CETANE IMPROVER FOR DIESEL FUEL

TECHNICAL FIELD

This invention relates to hydrocarbon-based fuels having improved ignition characteristics and a method of improving the ignition characteristics of such fuels. More particularly, the invention relates both to a method of enhancing the ignition and combustion characteristics, or cetane ratings, of diesel fuels by the addition of a treating agent and to the resulting compositions.

BACKGROUND ART

Hydrocarbon distillates and residual-containing oils having characteristics which render them otherwise suitable for use as fuels for compression ignition or diesel engines, or other atomizing or vaporizing type burners, frequently have ignition characteristics that render them unsuitable or only poorly suitable for such use. Fuels that have poor ignition characteristics, that is, relatively high spontaneous ignition temperatures, will exhibit an unduly large ignition lag between the time the fuel is injected into a zone of combustion and the time when the fuel ignites. In diesel engines, for example, a large ignition lag will result in combustion of the fuel and the development of pressure over an improper portion of the crank angle period and piston stroke, resulting in knocking, rough engine operation, incomplete combustion in the combustion zone, power loss, and ultimately detriment to the engine.

To overcome these ignition or combustion problems, the fuel may be refined to produce a higher proportion of straight chain hydrocarbons similar to the original industry standard, cetane. This is, however, costly and various treating agents, such as octyl nitrate, have been used to improve ignition and combustion characteristics. The ignition quality of a diesel fuel is normally expressed in terms of its cetane number. The cetane number of a given fuel is defined as the percent proportion of cetane (a fast burning $C_{16}$ paraffinic constituent) in alphamethyl-napthtalene (a slow burning aromatic material) that will match the performance of the fuel at the same compression ratio in a standard test engine.

DISCLOSURE OF INVENTION

The present invention relates to petroleum or hydrocarbon-based fuel compositions, particularly those in the diesel boiling range, that possess enhanced ignition quality and other performance characteristics and which are, therefore, better adapted for use in diesel engines and other atomizing or vaporizing type burners. By "diesel fuels", "fuel compositions boiling in the diesel range", or similar language, is meant those petroleum fractions from which the fuel is derived which are useful as fuel oil, gas oil and diesel oil and which distill above the kerosene fraction and below the lubricating oil fraction, that is, between about 250 degrees C. and about 400 degrees C. It has been found that such improved hydrocarbon-based fuel compositions can be obtained by incorporating into the fuel a small amount of at least one nitrate ester having the following general formula:

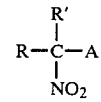

where
R is H, CH$_3$ or A;
R' is H, CH$_3$ or C$_2$H$_5$;
A is

or is

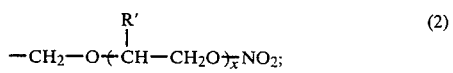

R" is H or C$_{1-3}$ alkyl; and
x is 1 or 2.

These nitrate esters of nitroalcohol derivatives are useful as fuel additives in that they contribute a high specific energy content which is liberated on combustion and thus provide useful kinetic energy at low cost. They have the further effect, in diesel fuels, of acting as cetane improvers by reducing the delay of ignition in the compression ignition engine.

The nitroalkyl nitrates and nitroalkoxy nitrates disclosed herein are employed in hydrocarbon-based fuels in an amount sufficient to improve the ignition quality or cetane rating of the fuel. This amount will vary somewhat according to the nature of the fuel, such as the base stock from which it is formed, and properties which may be varied by refining of the fuel. These cetane improving agents may be added to diesel fuel fractions as single components or a mixture of several of these agents may be used. Normally, a noticeable improvement in the ignition quality of a fuel oil will be obtained by incorporating therein as little as about 0.02 percent by volume of the nitroalkyl or nitroalkyl ether nitrate esters of this invention and the use of about 0.15 to about 0.30 percent by volume will result in a marked improvement. The improvement in cetane rating per unit volume increment of the nitrate esters of this invention gradually declines somewhat at proportions in the range of about 0.5 to about 1 percent by volume. The rate of decline in improvement per unit increment is greater at proportions in excess of 0.6 percent by volume so that little additional improvement with respect to ignition quality is obtained by the use of proportions in excess of 0.6 percent by volume.

The nitrate esters of the present invention conforming to the above general formula can be employed as cetane improving agents wherein each of the alkyl groups designated by R, R' and R" include a greater number of carbon atoms than represented above. However, as the size of the molecule and the carbon content increase much beyond what is defined by the general formula and associated radical designations indicated above, the improvement in cetane rating diminishes. In general, as the carbon content decreases, the cetane rating improvement increases. However, with very small molecules or those containing relatively small amounts of carbon, safety hazards due to the relatively explosive character of some of the compounds increase substantially. Thus, the compounds represented by the above general formula and defined pendant radicals represent compromises between optimum cetane improvement and practical handling and storage considerations of the cetane improving agents themselves.

The nitroalkyl and nitroalkoxy nitrate esters of the present invention can be prepared in any convenient manner. Thus, in those compounds in which A is

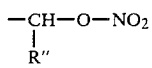

and R and R' are both $CH_3$, 2-nitropropane may be reacted with an appropriate aldehyde, such as acetaldehyde, propionaldehyde, or a butyraldehyde, in the presence of a base, to form the corresponding secondary nitroalcohol according to the reaction:

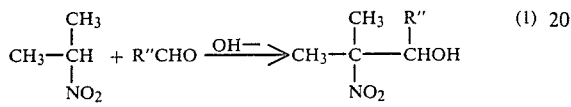

where R" is H or $C_{1-3}$ alkyl.

The nitroalcohol formed in this reaction can then be esterified under conditions which approximate those conventionally employed in esterifying an alcohol with nitric acid (using somewhat milder conditions with regard to the concentration of nitric acid and to temperature).

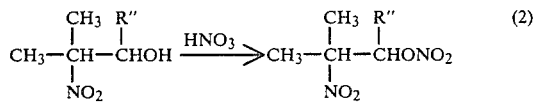

The nitroalkoxy nitrate esters, those compounds in which A is $CH_2O-(CHR'-CH_2O)_x-NO_2$, may be prepared by any convenient method. The preferred synthetic route starts with the appropriate nitroalcohol which may, in turn, be formed in the manner illustrated in reaction (1) above for the formation of the 1-substituted-2-nitro-2-methyl-1-propanol. The corresponding alkoxy alcohol may be obtained by reaction of the nitro alcohol with an alkylene oxide. For the cetane improving agents of the present invention, ethylene and propylene oxides are preferred. Conditions are selected in order to introduce either one or two molecules of alkylene oxide into each molecule of nitroalcohol according to the following reaction:

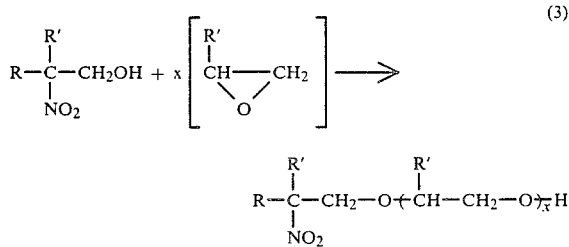

where x is 1 or 2 and R and R' have the same meaning as above.

Thereafter the nitroalkoxy alcohol ether may be esterified with nitric acid using somewhat milder conditions with regard to temperature and concentrations, as is normally applied to the esterification of aliphatic alcohols.

The cetane improving agents of the present invention can be incorporated in the hydrocarbon-based fuels disclosed herein in any suitable manner. These materials are normally soluble in paraffinic as well as aromatic hydrocarbons in the proportions disclosed herein and, therefore, can be incorporated directly in the fuels. However, since the cetane improving agents of the present invention are normally used in very small amounts, it may be preferable from the standpoint of rapidly facilitating formation of a homogeneous mixture and also from the aspect of accurately measuring the correct proportions, to employ the cetane improving agents in the form of a concentrated or stock solution in either a solvent which is compatible with the fuel, or the fuel itself.

The following examples further illustrate this invention. However, the invention should not be construed as being limited to or restricted in any way by these examples.

EXAMPLE 1: Preparation of 3-Methyl-3-Nitro-2-Butyl Nitrate

The precursor nitroalcohol compound 3-methyl-3-nitro-2-butanol can be prepared as follows: 88.10 grams of acetaldehyde mixed with 88.10 grams of ethanol (previously cooled in refrigerator) was added dropwise to 178.2 grams of 2-nitropropane in 100 ml of ethanol and 4 ml of NaOH. After about two-thirds of this acetaldehyde-ethanol addition charge was added, 4 ml of 10N NaOH and 15 ml of $H_2O$ were added to the reaction mixture. The remaining addition charge was then added dropwise to the reaction mixture as before. After being stirred one hour at room temperature, the reaction contents were transferred to a two liter distilling flask with magnetic stirring and c.w. condenser. A heating mantle was used, and the temperature adjusted to 35° C. At the end of a two-day period, the temperature had reached 39° C., and the heating mantle was shut off. Stirring of the reaction mixture continued. At the end of another two-day period, the temperature had fallen to 24° C. The pH of the reaction mixture was adjusted to 6.7 with 21 ml of a 9 gram 37% HCl in 68 ml $H_2O$ solution. The next day, the pH was found to still be at 6.7. Vacuum distillation with a hot water bath, vigoro tube, c.w. condenser, ice-chilled receiver, and dry ice trap was then begun. Heads came off from 50 mm pressure and 25° C. (pot temperature) through 3 mm pressure and 40° C. (pot temperature). The solution had turned blue-green, but nearly all of the color was removed with the heads in a first removed fraction of 265 ml. A second fraction of 27.53 grams was removed with a pot temperature of 66° C., a head temperature of 48° C., and 2 mm pressure. A third fraction of 86.11 grams of a slightly viscous liquid was removed at a pot temperature of 69° C., a head temperature of 55°–58° C., and 2 mm pressure. The second and third fractions were combined and found to be 85–86% pure 3-nitro-3-methyl-2-butanol by gas chromatography.

The 3-methyl-3-nitro-2-butyl nitrate of the present invention is prepared using 3-methyl-3-nitro-2-butanol as follows.

3-methyl-3-nitro-2-butanol, 20 grams, was added to a mixture of 120 grams of concentrated sulfuric acid and 39 grams of 90% nitric acid at 8°–10° C. over a ½ hour period and then stirred for an additional 20 minutes at 8°

C. The mixture was added dropwise to 800 ml of ice water with the temperature rising to 12° C.

Diesel fuel, 200 grams, was added, and the mixture was stirred for 20 minutes and phase separated. There was a considerable emulsion at the interface, and only 162 grams of clear organic phase was obtained. A second extraction with 200 grams of diesel fuel gave 257 grams of organic phase, and a third 200 gram diesel fuel extraction gave 201 grams. The total weight increase in the organic phase was 21 grams.

The combined organic phase was washed with 2×200 ml of water and phased, with the water/organic interface removed with the water. The total recovery of organic phase was 608 grams. The final organic phase was allowed to settle for ½ hour to allow any remaining water to separate. The water was then removed, and the organic phase contains the 3-methyl-3-nitro-2-butyl nitrate was then diluted with 6800 ml of diesel fuel.

EXAMPLE 2: Preparation of 2-Methyl-2-Nitro-3-Pentyl Nitrate

The precursor nitroalcohol compound 2-methyl-2-nitro-3-pentanol can be prepared as follows: 116.16 grams of propionaldehyde was added dropwise to 178.2 grams of 2-nitropropane in 100 ml of ethanol and 4 ml of NaOH. The temperature of the reaction mixture was maintained at 30°–35° C. After about two-thirds of the propionaldehyde was added, 4 ml of NaOH and 15 ml of $H_2O$ were added to the reaction mixture. After the addition of propionaldehyde was completed, the reaction mixture was transferred to a one liter distilling flask with magnetic stirring and c.w. condenser. A heating mantle was used, and the temperature adjusted to 35°–40° C. At the end of a three-day period, the temperature was at 39° C., and the heating mantle was shut off. Stirring of the reaction mixture continued. At the end of another three-day period, the temperature had fallen to 24° C. The pH of the reaction mixture was adjusted to 6.7 with 13 ml of a 9 gram 37% HCl in 68 ml $H_2O$ solution. Distillation was then begun. The first fraction of 158 ml was removed at 70 mm pressure and 45° C. (head temperature). A second fraction of 22 ml with two layers was removed at 50 mm pressure and 50° C. (head temperature). The third fraction of 41.52 grams was removed at a pot temperature of 71° C. and a head temperature of 55° C. The third fraction was found to contain 2-methyl-2-nitro-3-pentanol.

The 2-methyl-2-nitro-3-pertyl nitrate of the present invention is prepared using 2-methyl-2-nitro-3-pentanol as follows.

2-nitro-2-methyl-3-pentanol, 20 grams, was added to a mixture of 120 ml of concentrated sulfuric acid and 40 grams of 90% nitric acid over a 30-minute period at 6°–9° C. After ½ hour the acid solution was added to 800 ml of ice water.

Diesel fuel, 203 grams, was added and the mixture stirred for ½ hour and phase separated. 222.5 grams of organic phase was obtained. Two successive washed with 200 grams of diesel fuel gave 399 grams indicating that all of the material was removed in the first wash. The combined organic phase was washed with 100 ml of water and phased. The weight of the final organic phase was 615 grams. This organic phase containing 2-methyl-2-nitro-3-pentyl nitrate was then combined with 6800 ml of diesel fuel.

EXAMPLE 3: Preparation of 5-Methyl-5-Nitro-3-oxo-1-Hexanol

To 150 grams of 2-methyl-2-nitro-1-propanol (which is commercially available from, e.g., Angus Chemical Co., Northbrook, Ill.), and 1.5 ml of boron trifluoride etherate at 85°–95° C. was added gaseous ethylene oxide. GC analysis showed a mixture of di, tri, tetra and penta oxyethylated product. This mixture was fractionated at 0.1 mm after first adding 2 grams of calcium hydroxide and filtering the product. Distillation gave 19.5 grams of product which contained 10% unreacted alcohol and 10% high boiling isomers.

This material was added slowly to 120 grams of concentrated sulfuric acid and 40% of nitric acid at 5° C. After about ⅔ of the material was added there was a noticeable exotherm which raised the pot temperature to 40° C. but it was cooled rapidly back to 10° C. in less than 5 minutes. There did not appear to be any further exotherm during addition of the final ⅓ of alcohol. The product was added slowly to 800 ml of ice water.

Diesel fuel, 200 grams, was added and the product did not appear to be very soluble forming a third layer at the interface. The weight of the organic phase was 198 grams. Two successive 200 gram washes with diesel fuel gave 208.8 grams and 205.2 grams of successive phase, respectively. A final wash with 150 grams of diesel fuel gave 153 grams. The total weight increase was 15 grams.

The combined 765 grams of organic phase was washed with 200 ml of water to yield 762 grams of organic phase. The final organic phase was allowed to settle for ½ hour to allow any remaining water to separate. The water was then removed, and the organic phase containing the 5-methyl-5-nitro-3-oxo-1-hexanol was then diluted with 6200 ml of diesel fuel.

EXAMPLE 4: Cetane Improvement Tests

In order to determine the effectiveness of the nitroalkyl and nitroalkoxy nitrate esters of the present invention as cetane improvers, the nitrate esters were incorporated in varying proportions in a base fuel having a predetermined cetane number of 50.0. Individual samples were prepared using this base diesel fuel, which fuel was admixed with the selected nitrate while other samples were prepared using the same concentrations of the standard industry cetane improver, octyl nitrate. Samples of the test diesel oil compositions containing nitroalkyl nitrate, nitroalkoxy nitrate or octyl nitrate were tested for cetane number under standard test procedure ASTM D613.

The improvement shown above by addition of the nitrate esters of the present invention over the test fuel is dramatic and unpredictable in this art.

Briefly, this test involves comparing the ignition quality of an unknown test fuel under standard operating conditions with the ignition quality of reference fuel blends having known cetane numbers. The test is carried out in a single cylinder diesel engine having a continuously variable compression ratio. During the test, the compression ratio is varied for the test fuel and the reference fuels to obtain a fixed "delay period", that is, the time interval between fuel injection and ignition. When the compression ratio that produces the fixed delay period for the test fuel has been determined to be between the compression ratios that will producde the same delay period for two reference fuel blends that differ by not more than five cetane numbers, the rating of the sample is calculated by interpolation.

The standard reference fuels are prepared from n-cetane and alpha-methylnaphthalene meeting ASTM standards. However, secondary petroleum distillate reference fuels that have been calibrated against the standard blends are normally used for routine testing. The following results were obtained by use of this procedure.

| Cetane Improving Agent | Cetane Rating At Concentrations, By Volume | |
|---|---|---|
| | 0.15% | 0.30% |
| None | 50.0 | 50.0 |
| Octyl Nitrate | 56.1 | 58.6 |
| 3-methyl-3-nitro-2-butyl nitrate | 59.4 | 62.8 |
| 2-methyl-2-nitro-3-pentyl nitrate | 58.9 | 62.5 |
| 5-methyl-5-nitro-3-oxo-1-hexanol | 55.6 | 58.7 |

The hydrocarbon-based fuel compositions of this invention may contain, in addition to the nitrate ester cetane improvers of the present invention, other additives to improve the fuels in one or more respects. For example, the fuel compositions of this invention may also contain oxidation inhibitors, anti-foam agents and other ignition quality or combustion improvement agents.

It will be apparent to those skilled in the art that many modifications and variations of the invention as described herein can be made without departing from the spirit or scope thereof. Accordingly, only such limitations should be imposed as are indicated in the claims appened hereto.

We claim:

1. A fuel composition comprising a major amount of a hydrocarbon-based fuel and a small amount of at least one nitrate ester having the formula:

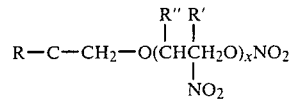

where
R is H, $CH_3$ or

R' is H, $CH_3$ or $C_2H_5$;
R" is H Or $C_{1-3}$ alkyl; and
x is 1 or 2
where said nitrate ester is present in an amount sufficient to produce an improvement in the cetane rating of said hydrocarbon-based fuel.

2. The fuel composition of claim 1 wherein said hydrocarbon-based fuel is a fuel boiling in the diesel range.

3. The fuel composition of claim 1 wherein said small amount is about 0.02 to about 1.0 percent by volume.

4. The fuel composition of claim 1 wherein said small amount is about 0.1 to about 0.5 percent by volume.

5. A method of improving the cetane rating of a hydrocarbon-based fuel comprising mixing with a hydrocarbon-based fuel of the diesel boiling range an amount of at least one nitrate ester having the formula:

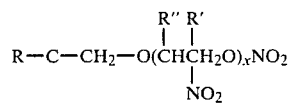

where
R is H, $CH_3$ or

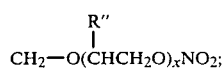

R' is H, $CH_3$ or $C_2H_5$;
R" is H or $C_{1-3}$ alkyl; and
x is 1 or 2
effective to produce an improvement in cetane rating of said hydrocarbon-based fuel.

6. The method according to claim 5 wherein said effective amount is about 0.02 to about 1.0 percent by volume.

* * * * *

UNITED STATES PATENT AND TRADEMARK OFFICE
CERTIFICATE OF CORRECTION

PATENT NO. : 4,549,883

DATED : October 29, 1985

INVENTOR(S) : Robert F. Purcell, Louis L. Hallock

It is certified that error appears in the above-identified patent and that said Letters Patent is hereby corrected as shown below:

On title page, Column 1, line 6, insert:

[73] Angus Chemical Company

Signed and Sealed this

Eighteenth Day of February 1986

[SEAL]

Attest:

Attesting Officer

DONALD J. QUIGG

Commissioner of Patents and Trademarks